United States Patent
Drewry et al.

(10) Patent No.: US 7,329,678 B2
(45) Date of Patent: Feb. 12, 2008

(54) CHEMICAL COMPOUNDS

(75) Inventors: David Harold Drewry, Durham, NC (US); Robert Neil Hunter, III, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 165 days.

(21) Appl. No.: 10/543,701

(22) PCT Filed: Jan. 27, 2004

(86) PCT No.: PCT/US2004/002076

§ 371 (c)(1),
(2), (4) Date: Jul. 28, 2005

(87) PCT Pub. No.: WO2004/069160

PCT Pub. Date: Aug. 19, 2004

(65) Prior Publication Data

US 2006/0148854 A1 Jul. 6, 2006

Related U.S. Application Data

(60) Provisional application No. 60/443,462, filed on Jan. 28, 2003, provisional application No. 60/452,335, filed on Mar. 5, 2003.

(51) Int. Cl.
*A61K 31/4439* (2006.01)
*C07D 401/04* (2006.01)

(52) U.S. Cl. .................................. 514/338; 546/273.4

(58) Field of Classification Search ............. 546/273.4; 514/338
See application file for complete search history.

(56) References Cited

U.S. PATENT DOCUMENTS 5,922,725 A 7/1999 Teuber et al.
6,416,759 B1 7/2002 Firestone et al.

FOREIGN PATENT DOCUMENTS

WO 01/25220 A 4/2001

OTHER PUBLICATIONS

Balant et al., "Metabolic Considerations, etc.," in Wolf. Burger's Medicinal Chemistry and Drug Discovery, NY: John Wiley and Sons, 5th edition, vol. 1, 1995, 949-982.*

* cited by examiner

*Primary Examiner*—Patricia L. Morris
(74) *Attorney, Agent, or Firm*—John L. Lemanowicz; Kathryn L. Coulter

(57) ABSTRACT

Benzimidazolyl-pyridine derivatives, which are useful as SGK-1 inhibitors are described herein. The described invention also includes methods of making such benzimidazolyl-pyridine derivatives as well as methods of using the same in the treatment of diseases mediated by inappropriate SGK-1 activity.

17 Claims, No Drawings

CHEMICAL COMPOUNDS

This application is filed pursuant to 35 U.S.C. § 371 as a United States National Phase Application of International Application No. PCT/US2004/002076 filed Jan. 27, 2004, which claims priority from U.S. 60/443,462 filed Jan. 28, 2003 and U.S. 60/452,335 filed Mar. 5, 2003.

BACKGROUND OF THE INVENTION

The present invention relates to benzimidazolyl-pyridine derivatives, compositions and medicaments containing the same, as well as processes for the preparation and use of such compounds, compositions and medicaments. Such benzimidazolyl-pyridine derivatives are useful in the treatment of diseases associated with inappropriate SGK-1 activity.

An important large family of enzymes is the protein kinase enzyme family. Currently, there are about 400 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

Serum and Glucocorticoid-Regulated Kinase 1 (SGK-1) is a serine/threonine protein kinase, whose function is thought linked to cell proliferation and electrolyte homeostasis. SGK-1 is a member of a family of intracellular kinases which includes protein kinase B. While it is transcriptionally induced by glucocorticoids and mineralocorticoids, it is activated by insulin and IGF-1 mediated phosphorylation through PI3-kinase and PDK-1. SGK-1 is thought to mediate several mechanisms, which contribute to disease states. As indicated above, IGF-1 activates SGK-1 and is involved in fibronectin synthesis, an element of renal fibrosis. Consequently, SGK-1 may mediate IGF-1 action on fibronectin synthesis. Insulin and IGF-1 also regulate Na$^+$ transport. The anti-diuretic aldosterone induces expression of SGK-1, which in turn activates the epithelial Na$^+$ channel thereby affecting Na$^+$ transport. Accordingly, SGK-1 may serve to mediate insulin, IGF-1, and aldosterone-induced Na$^+$ retention in renal and cardiovascular disease. SGK-1 may also mediate repair processes involving cell proliferation, for instance, through thrombin. Thrombin causes renal cell proliferation and increases SGK-1 expression in renal cells. Therefore, SGK-1 may provide a novel therapy for the regulation of electrolyte balance in renal and cardiovascular disease and in damaging cell proliferation in renal disease.

The present inventors have discovered novel benzimidazolyl-pyridine compounds, which are inhibitors of SGK-1 activity. Such benzimidazolyl-pyridine derivatives are useful in the treatment of disorders associated with inappropriate SGK-1 activity.

BRIEF SUMMARY OF THE INVENTION

In one aspect of the present invention, there is provided a compound of Formula (I):

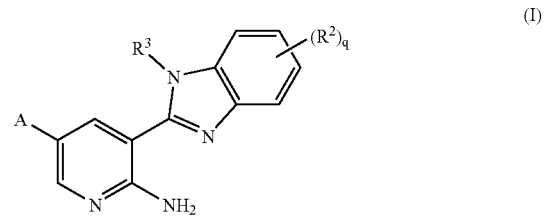

or a salt, solvate, or physiologically functional derivative thereof:

wherein:

A is aryl;

R$^2$ is —H, halo, C$_1$-C$_6$ alkyl, C$_1$-C$_6$ alkoxy, heteroaryl, —S(O)$_2$NR$^4$R$^5$, —C(O)OR$^6$, or —C(O)NR$^4$R$^5$;

q is 1, 2, 3, or 4;

R$^3$ is —H or C$_1$-C$_3$ alkyl;

R$^4$ is —H or C$_1$-C$_3$ alkyl;

R$^5$ is —H or C$_1$-C$_3$ alkyl; or

R$^4$ and R$^5$ together with the nitrogen to which they are attached form a heterocyclyl ring, said ring optionally containing 1 or 2 additional oxygen, S(O)$_m$, or nitrogen atoms; said nitrogen atoms being optionally substituted by a C$_1$-C$_3$ alkyl group;

m is 0, 1, or 2; and

R$^6$ is C$_1$-C$_6$alkyl

In a second aspect of the present invention, there is provided a compound of Formula (I):

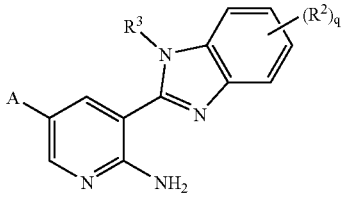

or a salt, solvate, or physiologically functional derivative thereof:

wherein:
A is aryl, optionally substituted with at least one $R^1$ group;
$R^1$ is $C_1$-$C_6$ alkyl, $C_1$-$C_6$ alkoxy, halo, —CN, —S(O)$_2$NR$^4$R$^5$, —C(O)NR$^4$R$^5$, or —N(H)C(O)NR$^4$R$^5$;
$R^2$ is —H, halo, $C_1$-$C_6$ alkyl, $C_1$-$C_6$ alkoxy, heteroaryl, —S(O)$_2$NR$^4$R$^5$, —C(O)OR$^6$, or —C(O)NR$^4$R$^5$;
q is 1, 2, 3, or 4;
$R^3$ is —H or $C_1$-$C_3$ alkyl;
$R^4$ is —H or $C_1$-$C_3$ alkyl;
$R^5$ is —H or $C_1$-$C_3$ alkyl; or
$R^4$ and $R^5$ together with the nitrogen to which they are attached form a heterocyclyl ring, said ring optionally containing 1 or 2 additional oxygen, S(O)$_m$, or nitrogen atoms; said nitrogen atoms being optionally substituted by a $C_1$-$C_3$ alkyl group;
m is 0, 1, or 2; and
$R^6$ is $C_1$-$C_6$ alkyl.

In a third aspect of the present invention, there is provided a compound of Formula (I):

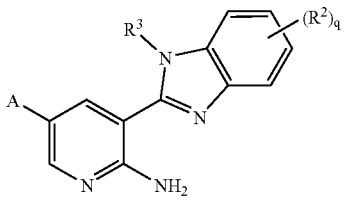

or a salt, solvate, or physiologically functional derivative thereof:

wherein:
A is aryl, optionally substituted with at least one $R^1$ group;
$R^1$ is $C_1$-$C_6$ alkyl, $C_1$-$C_6$ alkoxy, halo, —CN, —S(O)$_2$NR$^4$R$^5$, —C(O)NR$^4$R$^5$, or —N(H)C(O)NR$^4$R$^5$;
$R^2$ is —H, halo, $C_1$-$C_6$ alkyl, $C_1$-$C_6$ haloalkyl, $C_1$-$C_6$ alkoxy, heteroaryl, —S(O)$_2$NR$^4$R$^5$, —C(O)OR$^6$, or —C(O)NR$^4$R$^5$;
q is 1, 2, 3, or 4;
$R^3$ is —H;
$R^4$ is —H or $C_1$-$C_3$ alkyl;
$R^5$ is —H or $C_1$-$C_3$ alkyl; or
$R^4$ and $R^5$ together with the nitrogen to which they are attached form a heterocyclyl ring, said ring optionally containing 1 or 2 additional oxygen, S(O)$_m$, or nitrogen atoms; said nitrogen atoms being optionally substituted by a $C_1$-$C_3$ alkyl group;
m is 0, 1, or 2; and
$R^6$ is $C_1$-$C_6$ alkyl.

In a fourth aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In a fifth aspect of the present invention, there is provided a method of treating a disorder in a mammal, said disorder being mediated by inappropriate SGK-1 activity, comprising: administering to said mammal a therapeutically effective amount of a compound of formula (I) or a salt, solvate or a physiologically functional derivative thereof.

In a sixth aspect of the present invention, there is provided a compound of formula (I), or a salt, solvate, or a physiologically functional derivative thereof for use in therapy.

In a seventh aspect of the present invention, there is provided the use of a compound of formula (I), or a salt, solvate, or a physiologically functional derivative thereof in the preparation of a medicament for use in the treatment of a disorder mediated by inappropriate SGK-1 activity.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, heterocyclyl, aminosulfonyl optionally substituted by alkyl, nitro, cyano, halo, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_3$ alkyl" and "$C_1$-$C_6$ alkyl" refer to an alkyl group, as defined above, containing at least 1, and at most 3 or 6 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, heteroaryl, heterocyclyl, aminosulfonyl optionally substituted by alkyl, nitro, cyano, halo, and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_6$ alkylene" refer to an alkylene group, as defined above, which contains at least 1, and at most 3 or 6, carbon atoms respectively. Examples of "$C_1$-$C_6$ alkylene" and "$C_1$-$C_6$ alkylene" groups useful in the present invention include, but are not limited to, methylene, ethylene, n-propylene, n-butylene, isopentylene, and the like.

As used herein, the term "halogen" refers to fluorine (F), chlorine (Cl), bromine (Br), or iodine (I) and the term "halo" refers to the halogen radicals: fluoro (—F), chloro (—Cl), bromo (—Br), and iodo (—I).

As used herein, the term "$C_1$-$C_6$ haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "cycloalkyl" refers to a non-aromatic cyclic hydrocarbon ring containing from 3 to 10 carbon atoms and which optionally includes a $C_1$-$C_6$ alkyl linker through which it may be attached. In a like manner the term "$C_3$-$C_7$ cycloalkyl" refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

As used herein the term "heterocyclic spiro ring system" or "heterocyclyl spiro ring system" refers to a ring system having a three to twelve-membered non-aromatic heterocyclic ring, being saturated or having one or more degrees of unsaturation, containing one or more heteroatom substitutions selected from S, S(O), S(O)$_2$, O, or N, and a further ring being a heterocyclic, or aryl, or heteroaryl, or cycloalkyl ring, said rings of said ring system having one atom in common and being optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$-$C_6$ perfluoroalkyl, multiple degrees of substitution being allowed. Examples of "heterocyclic spiro ring systems" moieties include, but are not limited to, triazaspiro[4.5]decan-4-one.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halo, heteroaryl, heterocyclyl, aryl optionally substituted with aryl, halo, $C_1$-$C_6$ alkyl, $C_1$-$C_6$ haloalkyl, or $C_1$-$C_6$ alkylsulfonyl, ureido, arylurea, alkylurea, cycloalkylurea, alkylthiourea, aryloxy, or aralkyloxy, multiple degrees of substitution being allowed. Examples of "aryl" groups include, but are not limited to, phenyl, 2-naphthyl, 1-naphthyl, biphenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl-3-isoxazolylmethyl, and 2-imidazolyl ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, $C_1$-$C_6$ perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of:

$C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, or $C_1$-$C_6$ perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is alkyl as defined above and the terms "$C_1$-$C_3$ alkoxy" and "$C_1$-$C_6$ alkoxy" refer to an alkoxy group as defined herein wherein the alkyl moiety contains at least 1, and at most 3 or 6, carbon atoms. Exemplary "$C_1$-$C_3$ alkoxy" and "$C_1$-$C_6$ alkoxy" groups useful in the present invention include, but are not limited to, methoxy, ethoxy, n-propoxy, isopropoxy, n-butoxy, and t-butoxy.

As used herein, the term "amino" refers to the group —$NH_2$.

As used herein the term "alkylamino" refers to the group —$NHR_a$ wherein $R_a$ is alkyl as defined above.

As used herein the term "arylamino" refers to the group —$NHR_a$ wherein $R_a$ is aryl as defined above.

As used herein the term "aralkylamino" refers to the group —$NHR_a$ wherein $R_a$ is an aralkyl group as defined above.

As used herein the term "aralkoxy" refers to the group $R_bR_aO$—, where $R_a$ is alkylene and $R_b$ is aryl or heteroaryl all as defined above.

As used herein the term "aryloxy" refers to the group $R_aO$—, where $R_a$ is aryl or heteroaryl both as defined above.

As used herein the term "ureido" refers to the group —$NHC(O)NH_2$

As used herein, the term "arylurea" refers to the group —$NHC(O)NHR_a$ wherein $R_a$ is aryl as defined above.

As used herein, the term "arylthiourea" refers to the group —$NHC(S)NHR_a$ wherein $R_a$ is aryl as defined above.

As used herein, the term "alkylurea" refers to the group —$NHC(O)NHR_a$ wherein $R_a$ is alkyl as defined above.

As used herein, the term "cycloalkylurea" refers to the group —$NHC(O)NHR_a$ wherein $R_a$ is cycloalkyl as defined above.

As used herein, the term "$C_3$-$C_7$ cycloalkoxy" refers to the group $R_aO$—, where $R_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group $R_aO$—, where $R_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —$NHS(O)_2R_a$ wherein $R_a$ is alkyl as defined above and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —$NHS(O)_2R_a$ wherein $R_a$ is aryl as defined above.

As used herein, the term "alkylcarboxyamide" refers to the group —$NHC(O)R_a$ wherein $R_a$ is alkyl, amino, or amino substituted with alkyl, aryl or heteroaryl as described above.

As used herein the term "alkylcarboxy" refers to the group —$C(O)R_a$ wherein $R_a$ is alkyl as described above.

As used herein, the term "oxo" refers to the group =O.

As used herein, the term "mercapto" refers to the group —SH.

As used herein, the term "carboxy" refers to the group —$C(O)OR_a$, wherein $R_a$ is H or alkyl as defined herein.

As used herein, the term "cyano" refers to the group —CN.

As used herein the term "cyanoalkyl" refers to the group —$R_aCN$ wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —$S(O)_2NH_2$.

As used herein, the term "carbamoyl" refers to the group —$OC(O)NHR_a$. where $R_a$ is hydrogen or alkyl as defined herein.

As used herein, the term "carboxamide" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "aroylamino" refers to the group $R_aC(O)NH$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O—$, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

It is to be understood that reference to compounds of formula (I) above, following herein, refers to compounds within the scope of formula (I) as defined above with respect to A, q, m, $R^1$, $R^2$, $R^3$, $R^4$, $R^5$, and $R^6$ unless specifically limited otherwise.

As recited above, A is aryl. It is understood that such aryl group may be substituted as indicated above in the definition for "aryl". In a preferred embodiment, A is aryl, substituted by at least one $R^1$, wherein $R^1$ is as defined above.

In one embodiment, A is aryl. In a preferred embodiment, A is phenyl or phenyl substituted by at least one $R^1$, more preferably A is phenyl substituted by at least one $R^1$. $R^1$ is as defined above.

In one embodiment, $R^1$ is $C_1$-$C_6$ alkoxy, halo, or —CN, preferably $R^1$ is methoxy, —CN, or —F, more preferably $R^1$ is methoxy.

In one embodiment, q is 1 or 2 and each $R^2$ is independently selected from —H, halo, $C_1$-$C_6$ alkyl, $C_1$-$C_6$ alkoxy, —S(O)$_2$NR$^4$R$^5$, or —C(O)OR$^6$; preferably q is 1 or 2 and each $R^2$ is independently selected from —H, halo, $C_1$-$C_6$ alkyl, —S(O)$_2$NR$^4$R$^5$, or —C(O)OR$^6$; more preferably q is 1 and $R^2$ is —F, —CH$_3$, —C(O)OCH$_3$, or —S(O)$_2$NH$_2$; most preferably q is 1 and $R^2$ is —S(O)$_2$NH$_2$. $R^4$, $R^5$, and $R^6$ are as defined above.

In one embodiment, $R^3$ is $C_1$-$C_3$ alkyl, preferably methyl. In a preferred embodiment $R^3$ is —H.

Specific examples of compounds of the present invention include the following:
3-(1H-benzimidazol-2-yl)-5-phenylpyridin-2-amine;
3-(6-methoxy-1H-benzimidazol-2-yl)-5-phenylpyridin-2-amine;
methyl 2-(2-amino-5-phenylpyridin-3-yl)-1H-benzimidazole-6-carboxylate;
2-(2-amino-5-phenylpyridin-3-yl)-1H-benzimidazole-6-sulfonamide;
3-(6-fluoro-1H-benzimidazol-2-yl)-5-phenylpyridin-2-amine;
3-(4-methyl-1H-benzimidazol-2-yl)-5-phenylpyridin-2-amine;
methyl 2-[2-amino-5-(3-methoxyphenyl)pyridin-3-yl]-1H-benzimidazole-6-carboxylate;
3-(1H-benzimidazol-2-yl)-5-(3-methoxyphenyl)pyridin-2-amine;
2-[2-amino-5-(3-methoxyphenyl)pyridin-3-yl]-1H-benzimidazole-6-sulfonamide;
5-(3-methoxyphenyl)-3-(4-methyl-1H-benzimidazol-2-yl)pyridin-2-amine;
3-(5-chloro-6-fluoro-1H-benzimidazol-2-yl)-5-(3-methoxyphenyl)pyridin-2-amine;
2-[2-amino-5-(3,4,5-trimethoxyphenyl)pyridin-3-yl]-1H-benzimidazole-6-sulfonamide;
2-[2-amino-5-(3-cyanophenyl)pyridin-3-yl]-1H-benzimidazole-6-sulfonamide;
2-[2-amino-5-(4-fluorophenyl)pyridin-3-yl]-1H-benzimidazole-6-sulfonamide;
2-[2-amino-5-(4-methoxyphenyl)pyridin-3-yl]-1H-benzimidazole-6-sulfonamide;
3-(6-fluoro-1H-benzimidazol-2-yl)-5-(4-fluorophenyl)-pyridin-2-amine; or
5-(4-fluorophenyl)-3-(4-methyl-1H-benzimidazol-2-yl)pyridin-2-amine; and or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of formula (I) and salts, solvates and physiological functional derivatives thereof, are believed to have utility in chronic renal disease, congestive heart failure, and cardiovascular remodeling as a result of inhibition of the protein kinase SGK-1.

The present invention thus also provides compounds of formula (I) and pharmaceutically acceptable salts or solvates thereof, or physiologically functional derivatives thereof, for use in medical therapy, and particularly in the treatment of disorders mediated by SGK-1 activity.

The inappropriate SGK-1 activity referred to herein is any SGK-1 activity that deviates from the normal SGK-1 activity expected in a particular mammalian subject. Inappropriate SGK-1 activity may take the form of, for instance, an abnormal increase in activity, or an aberration in the timing and or control of SGK-1 activity. Such inappropriate activity may result then, for example, from overexpression or mutation of the protein kinase leading to inappropriate or uncontrolled activation.

The present invention is directed to methods of regulating, modulating, or inhibiting SGK-1 for the prevention and/or treatment of disorders related to unregulated SGK-1 activity. In particular, the compounds of the present invention can also be used in the treatment of certain forms of renal and cardiovascular disease as well as congestive heart failure.

A further aspect of the invention provides a method of treatment of a mammal suffering from a disorder mediated by SGK-1 activity, which includes administering to said subject an effective amount of a compound of formula (I) or a pharmaceutically acceptable salt, solvate, or a physiologically functional derivative thereof. In a preferred embodiment, the disorder is a susceptible cancer.

A further aspect of the present invention provides the use of a compound of formula (I), or a pharmaceutically acceptable salt or solvate thereof, or a physiologically functional derivative thereof, in the preparation of a medicament for the treatment of a disorder characterized by SGK-1 activity.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (I) can be prepared according to the synthetic sequences illustrated in Schemes 1 and 2 and further detailed in the Examples section following. The schemes are depicted using the embodiment wherein A is phenyl or substituted phenyl. $R^1$, $R^2$, and $R^3$ are as described above.

Scheme 1

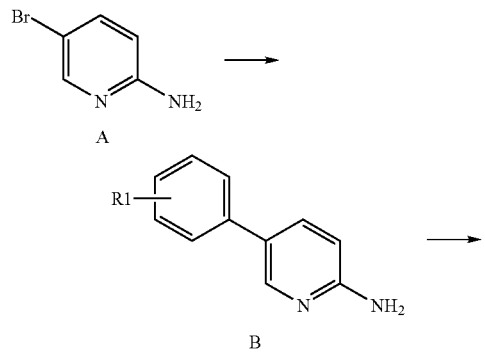

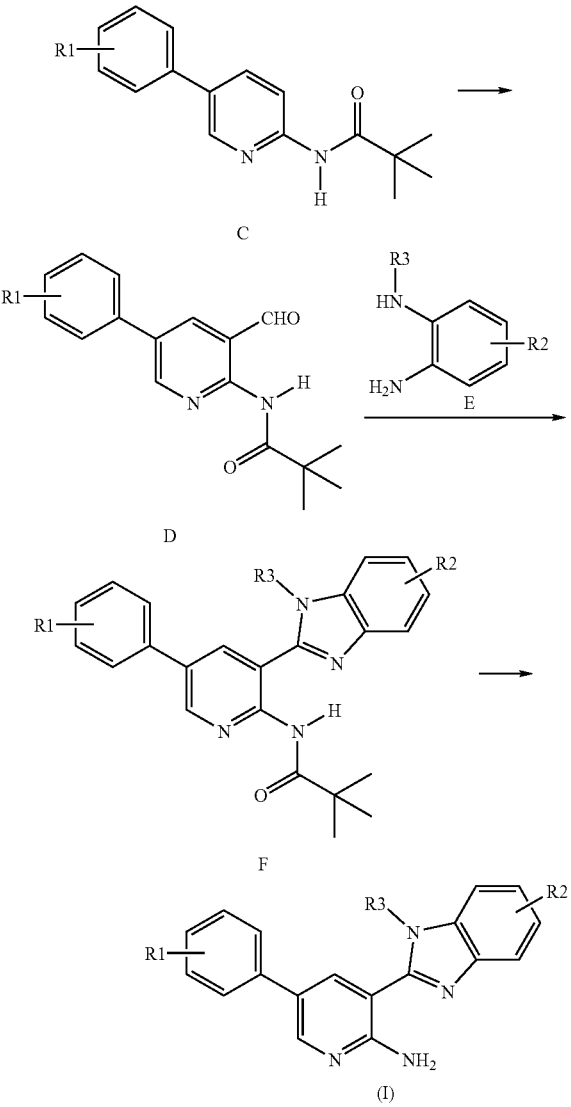

As illustrated in Scheme 1, compounds of formula (I) may be synthesized by deprotection of a functionalized pyridine such as depicted in F. The pivaloyl group illustrated as a nitrogen-protecting group in Scheme 1 may be removed, for example, by treatment with hydrochloric acid, or other methods known to one skilled in the art. Other suitable nitrogen protecting groups may also be employed in this synthetic scheme.

Compounds of formula F can be prepared by reaction of an aldehyde of formula D with a phenylenediamine of formula E in an appropriate solvent at temperatures between 30 and 250° C., often in the presence of an appropriate additive. For example, heating an appropriate aldehyde D, appropriate phenylenediamine E and NaHSO$_3$ in dimethylacetamide at 200° C. in a microwave instrument for 10 minutes provides compounds of formula F.

As is known to those skilled in the art, compounds of formula E are commercially available, or may be synthesized by standard literature methods.

Compounds of formula D may be synthesized by reaction of compounds of formula C with a strong base such as n-BuLi or t-BuLi in a solvent such as THF or dioxane, followed by reaction of the intermediate organometallic species with any of a number of appropriate formulating reagents such as dimethylformamide. Other nitrogen protecting groups known by those skilled in the art as useful for directed ortho-metallation may be used in place of the pivaloyl moiety depicted in Scheme 1.

Compounds of formula C can be synthesized by standard synthetic methods known to those skilled in the art to be useful for the incorporation of a nitrogen-protecting group. For example, reaction of an appropriate substituted amino pyridine of formula B with pivaloyl chloride and triethylamine in a solvent such as methylene chloride yields compounds of formula C.

Compounds of formula B may be synthesized by reaction of 2-amino-5-bromo-pyridine A with an aryl tin species or an aryl boronic acid species in an appropriate solvent in the presence of an appropriate catalyst and an appropriate base at a temperature between 30° C. and 250° C. These reactions (Suzuki reaction with an aryl boronic acid and Stille reaction with an aryl tin reagent) are well described in the literature, and a number of catalyst, base, solvent, and temperature combinations have proven useful. For example, heating 2-amino-5-bromo-pyridine with an aryl boronic acid, aqueous sodium carbonate and dichlorobis(triphenylphosphine) palladium (II) in dimethoxyethane at 150° C. for 10 minutes in a SmithSynthesizer™ microwave instrument is one method useful for synthesis of products of formula B.

Compound of formula J may be synthesized by reaction of 2-amino-3-formyl-5-bromo-pyridine with an aryl tin species or an aryl boronic acid species in an appropriate solvent in the presence of an appropriate catalyst and an appropriate base at a temperature between 30° C. and 250° C. These reactions (Suzuki reaction with an aryl boronic acid and Stille reaction with an aryl tin reagent) are well described in the literature, and a number of catalyst, base solvent, and temperature combinations have proven useful. For example, heating 2-amino-3-formyl-5-bromo-pyridine with an aryl boronic acid, aqueous sodium carbonate and dichlorobis(triphenylphosphine) palladium (II) in dimethoxyethane at 150° C. for 10 minutes in a SmithSynthesizer™ microwave instrument is one method useful for synthesis of products of formula J.

Compound H, 2-amino-3-formyl-5-bromo-pyridine, can be synthesized by reaction of compound G, 2-amino-3-formyl-pyridine, with a brominating reagent in an appropriate solvent. For example, the reaction can be accomplished by brominating with bromine in diethyl ether.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

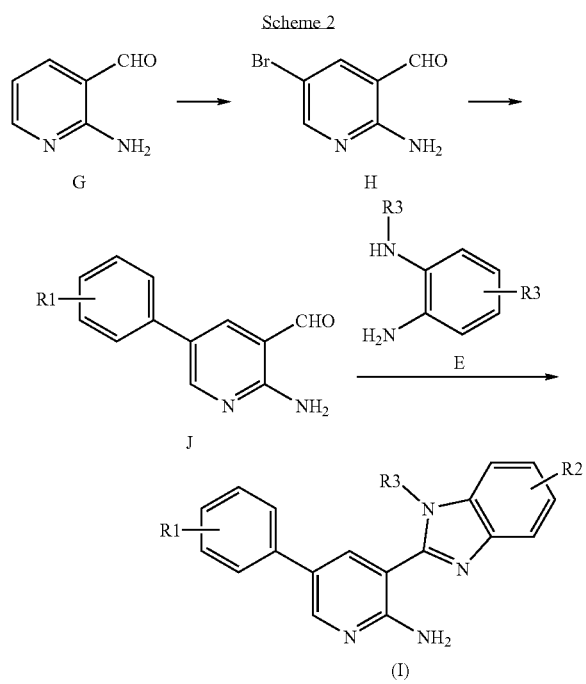

As depicted in Scheme 2, compounds of general formula (I) may also be synthesized by reaction of an aldehyde of formula J with a phenylenediamine of formula E in an appropriate solvent at temperatures between 30 and 250° C., often in the presence of an appropriate additive. For example, heating an appropriate aldehyde 3, appropriate phenylenediamine E and NaHSO$_3$ in dimethylacetamide at 200° C. in a SmithSynthesizer™ microwave instrument for 10 minutes provides compounds of formula (I). Again, R$^1$, R$^2$, and R$^3$ are as described above.

| | |
|---|---|
| g | (grams); |
| L | (liters); |
| μL | (microliters); |
| M | (molar); |
| i.v. | (intravenous); |
| MHz | (megahertz); |
| mmol | (millimoles); |
| min | (minutes); |
| mp | (melting point); |
| T$_r$ | (retention time); |
| MeOH | (methanol); |
| TEA | (triethylamine); |
| TFAA | (trifluoroacetic anhydride); |
| DMSO | (dimethylsulfoxide); |
| DME | (1,2-dimethoxyethane); |
| DCE | (dichloroethane); |
| DMPU | (N,N'-dimethylpropyleneurea); |
| IBCF | (isobutyl chloroformate); |
| HOSu | (N-hydroxysuccinimide); |
| mCPBA | (meta-chloroperbenzoic acid); |
| EDC | (1-[(3-dimethylamino) propyl]-3-ethylcarbodiimide hydrochloride); |
| BOC | (tert-butyloxycarbonyl); |
| DCC | (dicyclohexylcarbodiimide); |
| Ac | (acetyl); |
| TMSE | (2-(trimethylsilyl)ethyl); |
| TIPS | (triisopropylsilyl); |
| DMAP | (4-dimethylaminopyridine); |
| mg | (milligrams); |
| mL | (milliliters); |

| | |
|---|---|
| psi | (pounds per square inch); |
| mM | (millimolar); |
| Hz | (Hertz); |
| mol | (moles); |
| rt | (room temperature); |
| h | (hours); |
| TLC | (thin layer chromatography); |
| RP | (reverse phase); |
| i-PrOH | (isopropanol); |
| TFA | (trifluoroacetic acid); |
| THF | (tetrahydrofuran); |
| AcOEt | (ethyl acetate); |
| DCM | (dichloromethane); |
| DMF | (N,N-dimethylformamide); |
| CDI | (1,1'-carbonyldiimidazole); |
| HOAc | (acetic acid); |
| HOBT | (1-hydroxybenzotriazole); |
| FMOC | (9-fluorenylmethoxycarbonyl); |
| CBZ | (benzyloxycarbonyl); |
| atm | (atmosphere); |
| TMS | (trimethylsilyl); |
| TBS | (t-butyldimethylsilyl); |
| BSA | (bovine serum albumin) |
| ATP | (adenosine triphosphate); |
| HRP | (horseradish peroxidase); |
| DMEM | (Dulbecco's modified Eagle medium); |
| HPLC | (high pressure liquid chromatography); |
| BOP | (bis(2-oxo-3-oxazolidinyl)phosphinic chloride); |
| TBAF | (tetra-n-butylammonium fluoride); |
| HBTU | (O-Benzotriazole-1-yl-N,N,N',-N'-tetramethyluroniumhexafluorophosphate). |
| HEPES | (4-(2-hydroxyethyl)-1-piperazine ethane sulfonic acid); |
| DPPA | (diphenylphosphoryl azide); |
| fHNO$_3$ | (fuming HNO$_3$); and |
| EDTA | (ethylenediaminetetraacetic acid). |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimadzu HPLC system by the following conditions. Column: 50×4.6 mm (id) stainless steel packed with 5 μm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A:100-0%, B:0-100%), 3.0-3.5 min (A: 0%, B: 100%), 3.5-3.7 min (A: 0-100%, B: 100-0%), 3.7-4.5 min (A: 100%, B: 0%); Detection: UV 254 nm; Injection volume: 3 μL.

Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

The exchangeable protons in the following examples, in particular for the hydochloride salts, are often quite broad, thus at times making it difficult to obtain meaningful integration and chemical shift data. Accordingly, such data was not included in the following NMR data.

Example 1

3-(1H-benzimidazol-2-yl)-5-phenylpyridin-2-amine hydrochloride

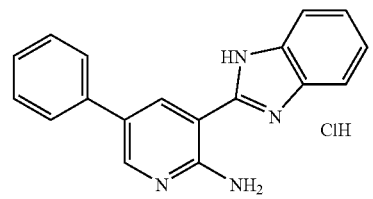

(a) preparation of 5-phenylpyridin-2-amine

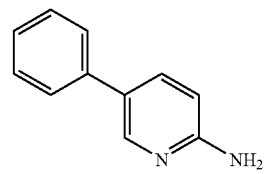

2-Amino-5-bromopyridine (5.0 g, 28.90 mmol), phenylboronic acid (7.05 g, 57.80 mmol), dichlorobis(triphenylphosphine)palladium(II) (1.01 g, 1.45 mmol), and 2M Na$_2$CO$_3$(aq) (24 mL, 48 mmol) were combined in 150 mL of dimethoxyethane and heated to reflux for 1 hour. Upon cooling, the reaction mixture was diluted with EtOAc and washed with H$_2$O and brine. The solvent was removed to give an amber oil which was chromatographed on silica gel eluting with hexanes/ethyl acetate (1:1) to afford 5-phenylpyridin-2-amine (2.42 g) as a tan solid.

1H NMR (300 MHz, DMSO-D6) δ ppm 6.04 (s, 2H) 6.51 (dd, J=8.64, 0.73 Hz, 1H) 7.25 (m, 1H) 7.38 (m, 2H) 7.54 (m, 2H) 7.68 (dd, J=8.57, 2.56 Hz, 1H) 8.23 (dd, J=2.56, 0.66 Hz, 1H) MS m/z 171 (M+1)$^+$.

(b) preparation of 2,2-dimethyl-N-(5-phenylpyridin-2-yl)propanamide

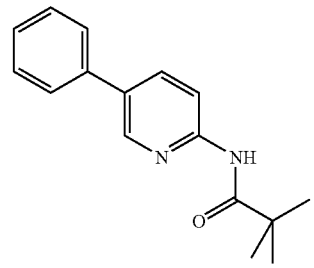

5-phenylpyridin-2-amine (2.4 g, 14.10 mmol) was dissolved in 75 ml of dichloromethane. The solution was treated with triethylamine (1.57 g, 15.51 mmol) and trimethylacetylchloride (1.87 g, 15.51 mmol) and the mixture was stirred at room temperature for 1 hour. Silica gel (9 g) was added and the solvent was removed in vacuo. The residue was chromatographed on silica gel eluting with hexanes/ethyl acetate (5:1) to afford 2,2-dimethyl-N-(5-phenylpyridin-2-yl)propanamide (2.58 g) as a white solid.

1H NMR (300 MHz, DMSO-D6) δ ppm 1.25 (s, 9H) 7.37 (m, 1H) 7.48 (m, 2H) 7.71 (m, 2H) 8.11 (m, 2H) 8.64 (dd, J=2.42, 0.66 Hz, 1H) 9.89 (s, 1H) MS m/z 255 (M+1)⁺.

(c) preparation of N-(3-formyl-5-phenylpyridin-2-yl)-2,2-dimethylpropanamide

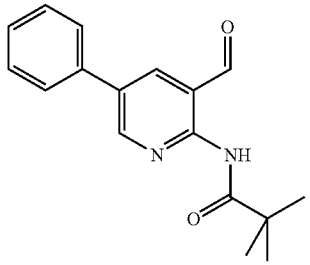

2,2-dimethyl-N-(5-phenylpyridin-2-yl)propanamide (2.5 g, 9.83 mmol) was dissolved in 80 mL of dry THF and cooled to 0° C. N-Butyl lithium (2.5 M in hexanes) (9.8 mL, 24.57 mmol) was added slowly. The reaction mixture was stirred at 0° C. for 2 hours and then N,N-dimethylformamide (3.6 g, 49.15 mmol) was added. The reaction mixture was removed from the cold bath and allowed to warm to room temperature. After 30 minutes the reaction was quenched with water. The mixture was extracted with EtOAc and dried over MgSO₄. The solvent was removed and the residue was chromatographed on silica gel eluting with hexanes/ethyl acetate (2:1) to afford N-(3-formyl-5-phenylpyridin-2-yl)-2,2-dimethylpropanamide (1.87 g).

1H NMR (400 MHz, DMSO-D6) δ ppm 1.28 (s, 9H) 7.45 (m, 1H) 7.52 (m, 2H) 7.79 (m, 2H) 8.38 (d, J=2.56 Hz, 1H) 8.97 (d, J=2.56 Hz, 1H) 9.76 (s, 1H) 10.53 (s, 1H) MS m/z 283 (M+1)⁺.

(d) preparation of N-[3-(1H-benzimidazol-2-yl)-5-phenylpyidin-2-yl]-2,2-dimethylpropanamide

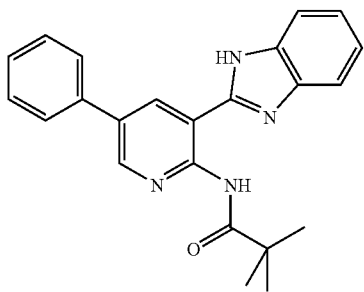

N-(3-formyl-5-phenylpyridin-2-yl)-2,2-dimethylpropanamide (0.1 g, 0.35 mmol), o-phenylenediamine (0.038 g, 0.35 mmol), and NaHSO₃ (0.039, 0.53 mmol) were combined in 3 mL of dimethylacetamide and heated to 250° C. in the SmithSynthesizer™ microwave instrument for 10 minutes. Upon cooling, the solvent was removed and the residue was chromatographed on silica gel eluting with hexanes/ethyl acetate (0 to 100% EtOAc over 20 minutes) to afford N-[3-(1H-benzimidazol-2-yl)-5-phenylpyridin-2-yl]-2,2-dimethylpropanamide (0.036 g). 1H NMR (400 MHz, DMSO-D6) δ ppm 1.37 (s, 9H) 7.32 (m, 2H) 7.45 (m, 1H) 7.56 (t, J=7.60 Hz, 2H) 7.65 (d, J=7.87 Hz, 1H) 7.72 (d, J=7.87 Hz, 1H) 7.86 (dd, J=8.33, 1.19 Hz, 2H) 8.81 (d, J=10.07 Hz, 2H) 12.87 (s, 1H) 13.38 (s, 1H) MS m/z 371 (M+1)⁺.

(e) preparation of 3-(1H-benzimidazol-2-yl)-5-phenylpyridin-2-amine hydrochloride N-[3-(1H-benzimidazol-2-yl)-5-phenylpyridin-2-yl]-2,2-dimethylpropanamide (0.036 g, 0.1 mmol) and 2 drops of HCl in 3 ml of EtOH was heated to 150° C. in the SmithSynthesizer™ microwave instrument for 10 minutes. Upon cooling the yellow solid was collected by vacuum filtration to afford 3-(1H-benzimidazol-2-yl)-5-phenylpyridin-2-amine hydrochloride (0.018 g).

1H NMR (400 MHz, DMSO-D6) δ ppm 7.33 (dd, J=6.04, 3.11 Hz, 2H) 7.45 (t, J=7.42 Hz, 1H) 7.55 (t, J=7.60 Hz, 2H) 7.71 (s, 2H) 7.84 (d, J=7.14 Hz, 2H) 8.53 (d, J=2.01 Hz, 1H) 9.11 (d, J=2.01 Hz, 1H) MS m/z 287 (M+1)⁺.

Example 2

3-(6-methoxy-1H-benzimidazol-2-yl)-5-phenylpyridin-2-amine hydrochloride

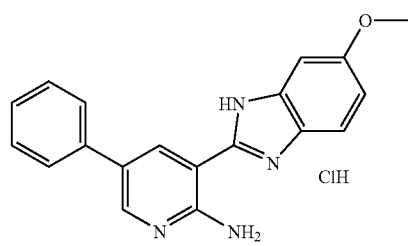

N-(3-formyl-5-phenylpyridin-2-yl)-2,2-dimethylpropanamide (0.075 g, 0.27 mmol) (see Example 1(c)), 4-methoxy-o-phenylenediamine (0.044 g, 0.32 mmol), and NaHSO₃ (0.029, 0.40 mmol) were combined in 3 mL of dimethylacetamide and heated to 200° C. in the SmithSynthesizer™ microwave instrument for 10 minutes. Upon cooling, the reaction mixture was diluted with 4 ml of H₂O. The solid was collected by vacuum filtration and rinsed with hexanes. The solid was combined with 20 μL of concentrated HCl in 3 ml of EtOH and heated to 150° C. in the SmithSynthesizer™ microwave instrument for 10 minutes. Upon cooling the green solid was collected by vacuum filtration to afford 3-(6-methoxy-1H-benzimidazol-2-yl)-5-phenylpyridin-2-amine hydrochloride (0.048 g).

1H NMR (300 MHz, DMSO-D6) δ ppm 3.83 (s, 3H) 6.94 (dd, J=8.72, 2.27 Hz, 1H) 7.14 (s, 1H) 7.43 (t, J=7.35 Hz, 1H) 7.56 (m, 3H) 7.83 (d, J=7.56 Hz, 2H) 8.49 (d, J=2.06 Hz, 1H) 9.07 (d, J=2.06 Hz, 1H) MS m/z 317 (M+1)⁺.

Example 3

Methyl 2-(2-amino-5-phenylpyridin-3-yl)-1H-benzimidazole-6-carboxylate hydrochloride

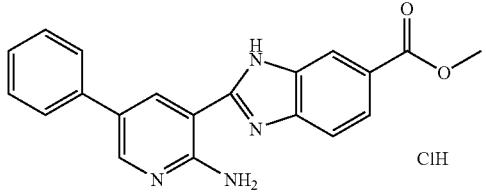

The title compound was synthesized using the procedure recited in Example 2, except that N-(3-formyl-5-phenylpyridin-2-yl)-2,2-dimethylpropanamide and methyl 3,4-diaminobenzoate were utilized.

1H NMR (300 MHz, DMSO-D6) δ ppm 3.89 (s, 3H) 7.44 (t, J=7.32 Hz, 1H) 7.55 (t, J=7.54 Hz, 2H) 7.83 (m, 3H) 7.94 (dd, J=8.50, 1.46 Hz, 1H) 8.29 (s, 1H) 8.57 (d, J=2.20 Hz, 1H) 9.11 (s, 1H) MS m/z 345 (M+1)$^+$

Example 4

2-(2-amino-5-phenylpyridin-3-yl)-1H-benzimidazole-6-sulfonamide hydrochloride

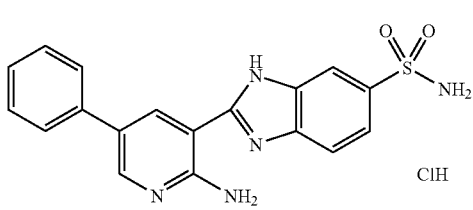

The title compound was synthesized using the procedure recited in Example 2, except that N-(3-formyl-5-phenylpyridin-2-yl)-2,2-dimethylpropanamide and 3,4-diaminobenzene-1-sulfonamide were utilized.

1H NMR (300 MHz, DMSO-D6) δ ppm 7.42 (m, 3H) 7.55 (t, J=7.62 Hz, 2H) 7.81 (m, 4H) 8.13 (s, 1H) 8.56 (d, 2.20 Hz, 1H) 8.88 (bs, 1H) 9.04 (d, J=1.90 Hz, 1H) MS m/z 364 (M−1)$^-$

Example 5

3-(6-fluoro-1H-benzimidazol-2-yl)-5-phenylpyridin-2-amine hydrochloride

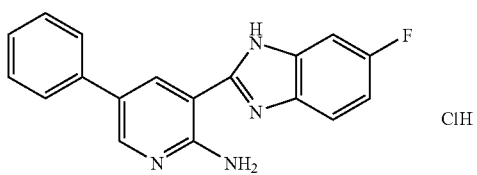

The title compound was synthesized using the procedure recited in Example 2, except that N-(3-formyl-5-phenylpyridin-2-yl)-2,2-dimethylpropanamide and 4-fluoro-o-phenylenediamine were utilized.

1H NMR (300 MHz, DMSO-D6) δ ppm 7.18 (m, 1H) 7.44 (t, J=7.25 Hz, 1H) 7.54 (m, 3H) 7.72 (dd, J=7.25, 4.17 Hz, 1H) 7.83 (m, 2H) 8.53 (d, J=2.20 Hz, 1H) 9.07 (d, J=2.05 Hz, 1H) MS m/z 305 (M+1)$^+$

Example 6

3-(4-methyl-1H-benzimidazol-2-yl)-5-phenylpyridin-2-amine hydrochloride

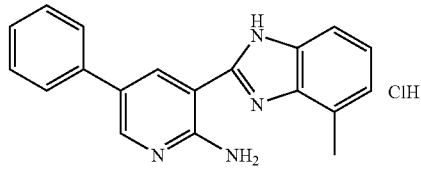

The title compound was synthesized using the procedure recited in Example 2, except that N-(3-formyl-5-phenylpyridin-2-yl)-2,2-dimethylpropanamide and 2,3-diaminotoluene were utilized.

1H NMR (300 MHz, DMSO-D6) δ ppm 2.62 (s, 3H) 7.12 (d, J=6.74 Hz, 1H) 7.22 (t, J=7.62 Hz, 1H) 7.50 (m, 4H) 7.82 (d, J=7.18 Hz, 2H) 8.51 (d, J=2.05 Hz, 1H) 9.08 (s, 1H) MS m/z 301 (M+1)$^+$.

Example 7

Methyl 2-[2-amino-5-(3-methoxyphenyl)pyridin-3-yl]-1H-benzimidazole-6-carboxylate hydrochloride

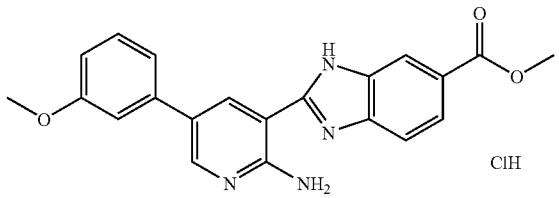

The title compound was synthesized using the procedure recited in Example 2, except that N-(3-formyl-5-(3-methoxyphenyl)pyridin-2-yl)-2,2-dimethylpropanamide and methyl 3,4-diaminobenzoate were utilized. N-(3-formyl-5-(3-methoxyphenyl) pyridin-2-yl)-2,2-dimethylpropanamide was synthesized using the sequence of steps (a), (b), and (c) of Example 1, utilizing 3-methoxyphenylboronic acid in step (a).

1H NMR (300 MHz, DMSO-D6) δ ppm 3.87 (s, 3H) 3.88 (s, 3H) 7.01 (m, 1H) 7.43 (m, 3H) 7.78 (d, J=8.64 Hz, 1H) 7.93 (dd. J=8.57, 1.54 Hz, 1H) 8.28 (s, 1H) 8.59 (d, J=2.05 Hz, 1H) 9.20 (d, J=1.90 Hz, 1H) MS m/z 375 (M+1)$^+$

Example 8

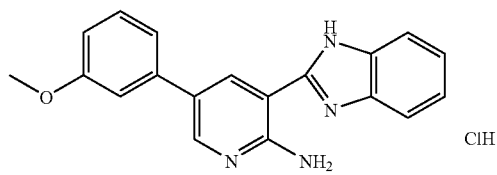

3-(1H-benzimidazol-2-yl)-5-(3-methoxyphenyl)pyridin-2-amine hydrochloride

The title compound was synthesized using the procedure recited in Example 2, except that N-(3-formyl-5-(3-methoxyphenyl)pyridin-2-yl)-2,2-dimethylpropanamide and ortho-phenylenediamine were utilized. N-(3-formyl-5-(3-methoxyphenyl)pyridin-2-yl)-2,2-dimethylpropanamide was synthesized using the sequence of steps (a), (b), and (c) of Example 1, utilizing 3-methoxyphenylboronic acid in step (a).

1H NMR (300 MHz, DMSO-D6) δ ppm 3.87 (s, 3H) 7.01 (m, 1H) 7.39 (m, 5H) 7.71 (dd, J=5.20, 3.74 Hz, 2H) 8.54 (d, J=2.20 Hz, 1H) 9.05 (s, 1H) MS m/z 317 (M+1)⁺

Example 9

2-[2-amino-5-(3-methoxyphenyl)pyridin-3-yl]-1H-benzimidazole-6-sulfonamide hydrochloride

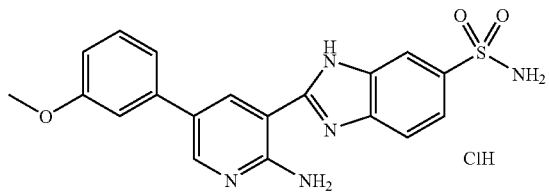

The title compound was synthesized using the procedure recited in Example 2, except that N-(3-formyl-5-(3-methoxyphenyl)pyridin-2-yl)-2,2-dimethylpropanamide and 3,4-diaminobenzene-1-sulfonamide were utilized. N-(3-formyl-5-(3-methoxyphenyl)pyridin-2-yl)-2,2-dimethylpropanamide was synthesized using the sequence of steps (a), (b), and (c) of Example 1, utilizing 3-methoxyphenylboronic acid in step (a).

1H NMR (300 MHz, DMSO-D6) δ ppm 3.87 (s, 3H) 7.01 (m, 1H) 7.42 (m, 5H) 7.78 (dd, J=8.64, 1.61 Hz, 1H) 7.85 (d, J=8.60 Hz, 1H) 8.14 (s, 1H) 8.59 (d, J=2.20 Hz, 1H) 9.12 (s, 1H) MS m/z 396 (M+1)⁺

Example 10

5-(3-methoxyphenyl)-3-(4-methyl-1H-benzimidazol-2-yl)pyridin-2-amine hydrochloride

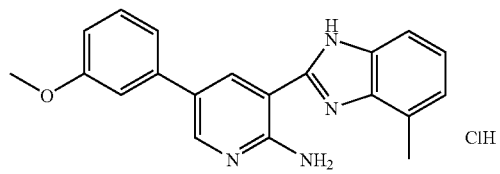

The title compound was synthesized using the procedure recited in Example 2, except that N-(3-formyl-5-(3-methoxyphenyl)pyridin-2-yl)-2,2-dimethylpropanamide and 2,3-diaminotoluene were utilized. N-(3-formyl-5-(3-methoxyphenyl)pyridin-2-yl)-2,2-dimethylpropanamide was synthesized using the sequence of steps (a), (b), and (c) of Example 1, utilizing 3-methoxyphenylboronic acid in step (a).

1H NMR (300 MHz, DMSO-D6) δ ppm 2.62 (s, 3H) 3.87 (s, 3H) 7.02 (d, J=7.62 Hz, 1H) 7.12 (d, J=7.32 Hz, 1H) 7.22 (t, J=7.69 Hz, 1H) 7.43 (m, 4H) 8.54 (d, J=2.20 Hz, 1H) 9.12 (s, 1H) MS m/z 331 (M+1)+

Example 11

3-(5-chloro-6-fluoro-1H-benzimidazol-2-yl)-5-(3-methoxyphenyl)pyridin-2-amine hydrochloride

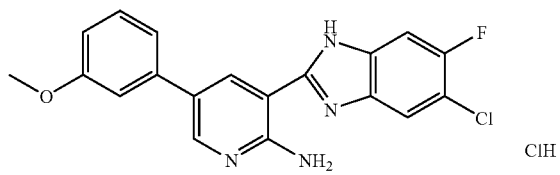

The title compound was synthesized using the procedure recited in Example 2, except that N-(3-formyl-5-(3-methoxyphenyl)pyridin-2-yl)-2,2-dimethylpropanamide and 1,2-diamino-4-chloro-5-fluorobenzene were utilized. N-(3-formyl-5-(3-methoxyphenyl)pyridin-2-yl)-2,2-dimethylpropanamide was synthesized using the sequence of steps (a), (b), and (c) of Example 1, utilizing 3-methoxyphenylboronic acid in step (a).

1H NMR (300 MHz, DMSO-D6) δ ppm 3.86 (s, 3H) 7.00 (d, J=9.52 Hz, 1H) 7.38 (m, 2H) 7.45 (t, J=8.06 Hz, 1H) 7.76 (d, J=8.79 Hz, 1H) 7.92 (d, J=5.57 Hz, 1H) 8.56 (d, J=2.05 Hz, 1H) 9.03 (d, J=1.90 Hz, 1H) MS m/z 369 (M+1)⁺

Example 12

2-[2-amino-5-(3,4,5-trimethoxyphenyl)pyridin-3-yl]-1H-benzimidazole-6-sulfonamide

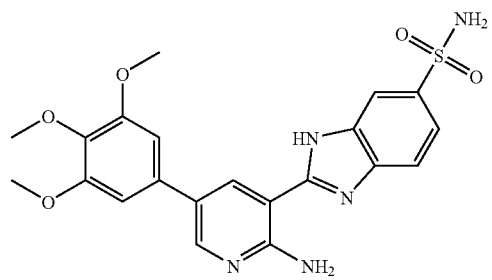

The title compound was synthesized using the procedure recited in Example 2, except that N-(3-formyl-5-(3,4,5-trimethoxyphenyl)pyridin-2-yl)-2,2-dimethylpropanamide and 3,4-diaminobenzene-1-sulfonamide were utilized. N-(3-formyl-5-(3,4,5-trimethoxyphenyl)pyridin-2-yl)-2,2-dimethylpropanamide was synthesized using the sequence of steps (a), (b), and (c) of Example 1, utilizing 3,4,5-trimethoxyphenylboronic acid in step (a).

1H NMR (300 MHz, DMSO-D6) δ ppm 3.69 (s, 3H) 3.89 (s, 6H) 6.98 (s, 2H) 7.30 (s, 1H) 7.36 (s, 1H) 7.84 (m, 5H) 8.52 (s, 2H) 13.31 (s, 1H) MS m/z 456 (M+1)⁺.

Example 13

2-[2-amino-5-(3-cyanophenyl)pyridin-3-yl]-1H-benzimidazole-6-sulfonamide

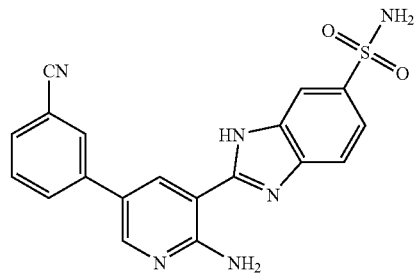

(a) preparation of 2-amino-5-bromonicotinaldehyde

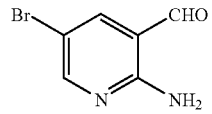

To a stirred solution of 2-aminopyridine-3-carboxaldehyde (10 g, 81.88 mmol) in dry diethyl ether, bromine (5.45 ml, 106.44 mmol) was added drop-wise. The reaction was stirred at ambient temperature for 30 min. The amber solids were filtered and dissolved in ethyl acetate. The ethyl acetate solution was washed with 1 N NaOH and then brine, dried over anhydrous Na₂SO₄ and filtered. The solvent was evaporated to afford 2-amino-5-bromonicotinaldehyde (14.6 g, 88% yield).

1H NMR (300 MHz, CD₃OD) δ ppm 7.69 (brs, 2H) 8.11 (d, J=2.5 Hz, 1H) 8.23 (d, J=2.5 Hz, 1H) 9.81 (s, 1H) MS m/z 202 (M+1)⁺

(b) preparation of 3-(6-amino-5-formylpyridin-3-yl)benzonitrile

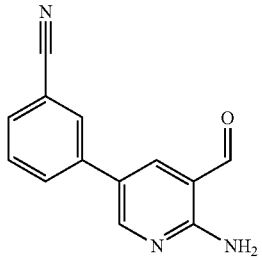

2-amino-5-bromonicotinaldehyde (0.1 g, 0.5 mmol), 3-cyanophenylboronic acid (0.146 g, 1.0 mmol), dichlorobis(triphenylphosphine)palladium(II) (0.017 g, 0.02 mmol), and K₂CO₃ (0.14 g, 1.0 mmol) were combined in 3 mL of 4:1 CH₃CN:H₂O and heated to 150° C. for 5 minutes in the SmithSynthesizer™ microwave instrument. Upon cooling, the reaction mixture was chromatographed on silica gel eluting with hexanes/ethyl acetate (0% EtOAc to 100% EtOAc over 10 minutes) to afford 3-(6-amino-5-formylpyridin-3-yl)benzonitrile (46 mg) as a solid.

1H NMR (400 MHz, DMSO-D6) δ ppm 7.66 (t, J=7.51 Hz, 1H) 7.79 (m, 3H) 8.06 (d, J=8.06 Hz, 1H) 8.22 (s, 1H) 8.51 (d, J=2.56 Hz, 1H) 8.71 (d, J=2.56 Hz, 1H) 9.96 (s, 1H) MS m/z 224 (M+1)⁺.

(c) preparation of 2-[2-amino-5-(3-cyanophenyl)pyridin-3-yl]-1H-benzimidazole-6-sulfonamide 3-(6-amino-5-formylpyridin-3-yl)benzonitrile (0.06 g, 0.27 mmol), 3,4-diaminobenzene-1-sulphonamide (0.050 g, 0.27 mmol), and NaHSO₃ (0.029, 0.40 mmol) were combined in 2 mL of dimethylacetamide and heated to 200° C. in the SmithSynthesizer™ microwave instrument for 10 minutes. Upon cooling, the solvent was removed and the residue was chromatographed on silica gel eluting with hexanes/ethyl acetate (0 to 100% EtOAc over 10 minutes) to afford 2-[2-amino-5-(3-cyanophenyl)pyridin-3-yl]-1H-benzimidazole-6-sulfonamide (0.046 g) as a solid.

1H NMR (400 MHz, DMSO-D6) δ ppm 7.30 (s, 1H) 7.37 (s, 1H) 7.74 (m, 4H) 7.87 (d, J=8.79 Hz, 1H) 7.99 (s, 1H) 8.13 (m, J=20.69 Hz, 2H) 8.23 (s, 1H) 8.61 (d, J=2.20 Hz, 1H) 8.67 (d, J=6.77 Hz, 1H) 13.36 (s, 1H) MS m/z 391 (M+1)⁺.

Example 14

2-[2-amino-5-(4-fluorophenyl)pyridin-3-yl]-1H-benzimidazole-6-sulfonamide

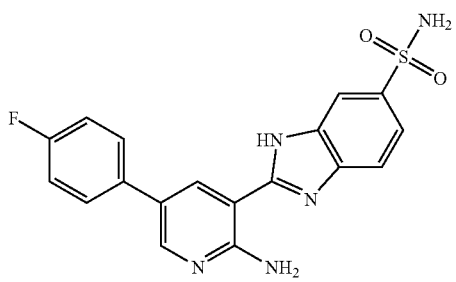

The title compound was synthesized using the procedure of step (c) in Example 13 except that 2-amino-5-(4-fluorophenyl)pyridin-3-carboxaldehyde and 3,4-diaminobenzene-1-sulfonamide were utilized. The 2-amino-5-(4-fluorophenyl)pyridin-3-carboxaldehyde was synthesized according to step (b) of example 13, using 4-fluorophenylboronic acid.

1H NMR (400 MHz, DMSO-D6) δ ppm 7.33 (m, 3H) 7.76 (m, 5H) 8.05 (m, 3H) 8.48 (d, J=2.01 Hz, 1H) 8.58 (dd, J=8.88, 1.92 Hz, 1H) 13.37 (s, 1H) MS m/z 384 (M+1)⁺.

Example 15

2-[2-amino-5-(4-methoxyphenyl)pyridin-3-yl]-1H-benzimidazole-6-sulfonamide

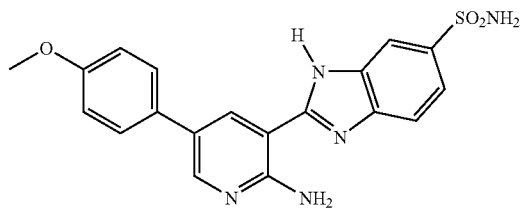

(a) 2-amino-5-(4-methoxyphenyl)nicotinaldehyde

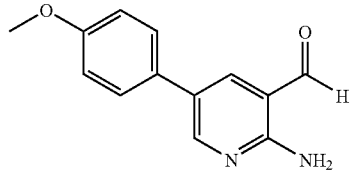

2-amino-5-bromonicotinaldehyde (1.61 g, 8 mmol), 4-methoxyphenylboronic acid (2.43 g, 16 mmol) and anhydrous potassium carbonate (2.21 g, 16 mmol) were dissolved in 50 ml of CH₃CN/H₂O (8:2), and 1 mol % of dichlorobis(triphenylphopsine)palladium(II) (56 mg, 0.08 mmol) was added while stirring. The reaction mixture was heated to reflux and stirred for 2 h. The reaction mixture was allowed to cool, and then partitioned between diethyl ether and water. The aqueous layer was extracted with another portion of diethyl ether. The combined organics were washed with brine, dried over anhydrous Na₂SO₄, filtered and concentrated in vacuo. The compound was purified by chromatography on silica gel eluting with with 30% EtOAc/hexanes to yield 2-amino-5-(4-methoxyphenyl)nicotinaldehyde (0.85 g, 47%).

1H NMR (300 MHz, d-DMSO) δppm 3.78 (s, 3H) 7.0 (d, 2H) 7.57 (s, 2H) 7.59 (d, 2H) 8.28 (d, J=2.7, 1H) 8.55 (d, J=2.7, 1H) 9.95 (s, 1H) MS m/z 229.21 (M+1)⁺

(b) 2-[2-amino-5-(4-methoxyphenyl)pyridin-3-yl]-1H-benzimidazole-6-sulfonamide 2-amino-5-(4-methoxyphenyl)nicotinaldehyde (61.6 mg, 0.27 mmol), 3,4-diaminobenzene-1-sulphonamide (59.7 mg, 0.32 mmol), and NaHSO₃ (29.2 mg, 0.4 mmol) were suspended in 3 ml dimethylacetamide. The reaction mixture was heated to 200° C. for 10 min in the SmithSynthesizer™ microwave instrument. Upon cooling, 5 ml of 4:1H₂O/EtOAc was added to afford a slurry which was stirred for 1 h. The solids were collected via vacuum filtration, washed with water and then diethyl ether, and dried under vacuum for 15 hours to yield 2-[2-amino-5-(4-methoxyphenyl)pyridin-3-yl]-1H-benzimidazole-6-sulfonamide (16 mg).

1H NMR (300 MHz, d-DMSO) δppm 3.82 (s, 3H), 7.08 (d, 2H), 7.35 (s 2H), 7.69 (d, 2H) 7.77 (m, 2H) 8.1 (s, 1H) 8.46 (d, J=2.3 Hz, 1H) 8.76 (d, J=2.3 Hz, 1H) MS m/z 396 (M+1)⁺

Example 16

3-(6-fluoro-1H-benzimidazol-2-yl)-5-(4-fluorophenyl)-pyridin-2-amine

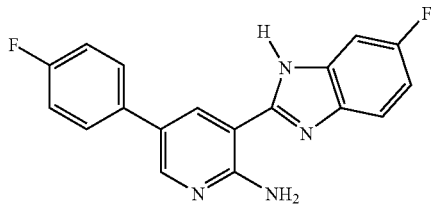

(a) preparation of 2-amino-5-(4-fluorophenyl)nicotinaldehyde

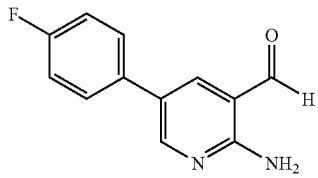

Using the procedure of step (a) in Example 15, utilizing 4-fluorophenylboronic acid gave 2-amino-5-(4-fluorophenyl)nicotinaldehyde (1.2 g, 93%).

1H NMR (300 MHz, d-DMSO) δppm 7.26 (m, 2H) 7.65 (s, 2H) 7.69 (m, 2H) 8.34 (d, J=2.5 Hz, 1H) 8.58 (d, J=2.5 Hz, 1H) 9.95 (s, 1H), MS m/z 217.16 (M+1)$^+$.

(b) preparation of 3-(6-fluoro-1H-benzimidazol-2-yl)-5-(4-fluorophenyl)-pyridin-2-amine Using the procedure of step (b) in Example 15, utilizing 2-amino-5-(4-fluorophenyl)nicotinaldehyde and 4-fluoro-o-phenylenediamine gave 3-(6-fluoro-1H-benzimidazol-2-yl)-5-(4-fluorophenyl)-pyridin-2-amine.

1H NMR (300 MHz, d-DMSO) δppm 7.12 (m, 1H) 7.34 (m, 2H) 7.45 (d, 1H) 7.65 (s, 1H) 7.77 (m, 2H) 8.20 (br s 2H) 8.45 (d, J=2.3 Hz, 1H) 8.63 (d, J=2.3 Hz, 1H) 13.2 (br s 1H) MS m/z 323.4 (M+1)$^+$

Example 17

5-(4-fluorophenyl)-3-(4-methyl-1H-benzimidazol-2-yl)pyridin-2-amine

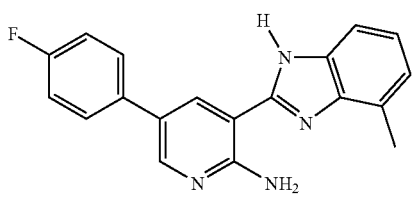

Using the procedure of step (b) in Example 15, utilizing 2-amino-5-(4-fluorophenyl)nicotinaldehyde and 2,3-diaminotoluene gave 5-(4-fluorophenyl)-3-(4-methyl-1H-benzimidazol-2-yl)pyridin-2-amine.

1H NMR (300 MHz, d-DMSO) δppm 2.61 (s, 3H) 7.06 (d, 1H) 7.15 (t, 1H) 7.37 (m, 2H) 7.47 (d, 1H) 7.8 (m, 2H) 8.45 (d, J=2 Hz, 1H) 8.78 (d, J=2 Hz, 1H) MS m/z 319.45 (M+1)$^+$

BIOLOGICAL DATA

SGK-1 Enzyme Assay (SGK1e):

Compounds of the present invention were tested for Serum Glucocorticoid-regulated Kinase-1 (SGK-1) protein serine/threonine kinase inhibitory activity in substrate phosphorylation assays using enzyme purified from a baculovirus expression vector system. The recombinant baculovirus was made to express the intracellular domain of SGK-1 (GenBank accession number AAD41091). The virus expressed a truncated form of the human enzyme that included amino acids 61-431. Serine 422 was replaced with Aspartic acid to activate the enzyme, and 6 Histidine residues were added at the amino terminus to facilitate purification. The protein was purified using Ni-NTA agarose affinity chromatography. The peptide substrate was an N-terminal biotinylated synthetic peptide named Crosstide (biotin-Ahx-GRPRTSSFAEG-OH), corresponding to the sequence in GSK3 surrounding the serine phosphorylated by MAPKAP Kinase-1/Rsk and p70 S6 Kinase.

The method measures the ability of the isolated enzyme to catalyze the transfer of the γ-phosphate from ATP onto serine/threonine residues in the biotinylated Crosstide. Reactions were performed in 96-well polystyrene round-bottom plates in a final volume of 30 μL. Reaction mixtures contained 62.5 mM HEPES (pH 7.4), 10 mM MgCl$_2$, 0.1 mM EDTA, 0.0024% TWEEN-20, and 1 mM DTT (added fresh daily), 10 μM ATP, 0.2 μCi [[γ-$^{33}$P] ATP per reaction, 4 μM Crosstide peptide substrate, and 1 nM SGK1 enzyme. Reactions were initiated by adding the indicated enzyme. The reaction was allowed to proceed for 2 hours, then terminated by the addition of 50 mM EDTA and quantified using a scintillation proximity assay procedure as described (McDonald, O. B., Antonsson, B., Arkinstal, S., Marshall, C. J., and Wood, E. R. (1999) *Analytical Biochemistry*, 268, 318-329).

Compounds under analysis were dissolved in Me$_2$SO to 1 mM and serially diluted 1 to 3 with Me$_2$SO through eleven columns of a 96 well plate. 1 μL of each concentration was transferred to the corresponding well of the assay plate. This created a final compound concentration range from 0.56 nM to 33.3 μM.

The data for dose responses were plotted as % Control calculated with the data reduction formula 100*(U1−C2)/(C1−C2) versus concentration of compound and fitted to the curve described by:

$$y = ((V\max * x)/(K+x))$$

where Vmax is the upper asymptote and K is the IC$_{50}$.

All exemplified Examples 1-17 were run with the recited assay and showed inhibitory activity versus SGK-1 with a pIC$_{50}$ of 4.0 or greater. Respresentative Examples are depicted in Table I.

TABLE I

| Ex. No | SGK1e |
|---|---|
| 1 | +++ |
| 4 | +++ |
| 7 | +++ |
| 11 | +++ |
| 14 | +++ |
| 17 | +++ |

+ = pIC$_{50}$ of 4.0-5.0;
++ = pIC$_{50}$ of 5.0-6.0;
+++ = pIC$_{50}$ of > 6.0;

We claim:
1. A compound of Formula (I):

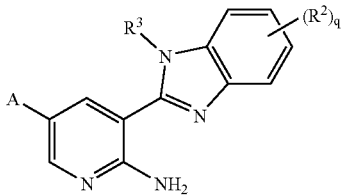

or a salt thereof:
wherein:
A is aryl;
R$^2$ is —H, halo, C$_1$-C$_6$ alkyl, C$_1$-C$_6$ alkoxy, —S(O)$_2$NR$^4$R$^5$, —C(O)OR$^6$, or —C(O)NR$^4$R$^5$;
q is 1, 2, 3, or 4;
R$^3$ is —H or C$_1$-C$_3$ alkyl;
R$^4$ is —H or C$_1$-C$_3$ alkyl;
R$^5$ is —H or C$_1$-C$_3$ alkyl; and
R$^6$ is C$_1$-C$_6$ alkyl.

2. A compound of formula (I):

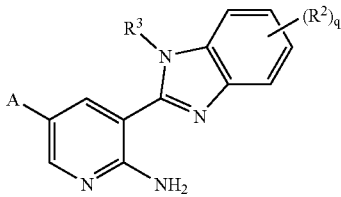

or a salt thereof:
wherein:
A is aryl, optionally substituted with at least one R$^1$ group;
R$^1$ is C$_1$-C$_6$ alkyl, C$_1$-C$_6$ alkoxy, halo, —CN, —S(O)$_2$NR$^4$R$^5$, —C(O)NR$^4$R$^5$, or —N(H)C(O)NR$^4$R$^5$;
R$^2$ is —H, halo, C$_1$-C$_6$ alkyl, C$_1$-C$_6$ alkoxy, —S(O)$_2$NR$^4$R$^5$, —C(O)OR$^6$, or —C(O)NR$^4$R$^5$;
q is 1, 2, 3, or 4;
R$^3$ is —H or C$_1$-C$_3$ alkyl;
R$^4$ is —H or C$_1$-C$_3$ alkyl;
R$^5$ is —H or C$_1$-C$_3$ alkyl; and
R$^6$ is C$_1$-C$_6$ alkyl.

3. A compound of Formula (I):

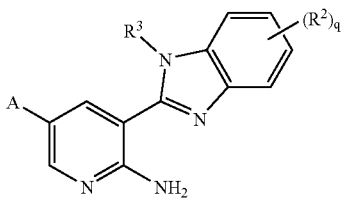

or a salt thereof:
wherein:
A is aryl, optionally substituted with at least one R$^1$ group;
R$^1$ is C$_1$-C$_6$ alkyl, C$_1$-C$_6$ alkoxy, halo, —CN, —S(O)$_2$NR$^4$R$^5$, —C(O)NR$^4$R$^5$, or —N(H)C(O)NR$^4$R$^5$;
R$^2$ is —H, halo, C$_1$-C$_6$ alkyl, C$_1$-C$_6$ haloalkyl, C$_1$-C$_6$ alkoxy, —S(O)$_2$NR$^4$R$^5$, —C(O)OR$^6$, or —C(O)NR$^4$R$^5$;
q is 1, 2, 3, or 4;
R$^3$ is —H;
R$^4$ is —H or C$_1$-C$_3$ alkyl;
R$^5$ is —H or C$_1$-C$_3$ alkyl; and
R$^6$ is C$_1$-C$_6$ alkyl.

4. A compound as claimed in claim 1, wherein A is phenyl.
5. A compound as claimed in claim 2, wherein A is phenyl substituted by at least one R$^1$, each R$^1$ being independently selected from C$_1$-C$_6$ alkoxy, halo, or —CN.
6. A compound as claimed in claim 5, wherein each R$^1$ is independently selected from methoxy, —CN, or —F.
7. A compound as claimed in claim 5, wherein each R$^1$ is methoxy.
8. A compound as claimed in claim 1, wherein q is 1 or 2 and each R$^2$ is independently selected from —H, halo, C$_1$-C$_6$ alkyl, C$_1$-C$_6$ alkoxy, —S(O)$_2$NR$^4$R$^5$, or —C(O)OR$^6$.
9. A compound as claimed in claim 1, wherein q is 1 or 2 and each R$^2$ is independently selected from —H, halo, C$_1$-C$_6$ alkyl, —S(O)$_2$NR$^4$R$^5$, or —C(O)OR$^6$.
10. A compound as claimed in claim 1, wherein q is 1 and R$^2$ is —F, —CH$_3$, —C(O)OCH$_3$, or —S(O)$_2$NH$_2$.
11. A compound as claimed in claim 1, wherein q is 1 and R$^2$ is —S(O)$_2$NH$_2$.
12. A compound as claimed in claim 1, wherein R$^3$ is C$_1$-C$_3$ alkyl.
13. A compound as claimed in claim 1, wherein R$^3$ is C$_1$-C$_3$ methyl.
14. A compound as claimed in claim 1, wherein R$^3$ is —H.
15. A compound selected from the group consisting of:
3-(1H-benzimidazol-2-yl)-5-phenylpyridin-2-amine;
3-(6-methoxy-1H-benzimidazol-2-yl)-5-phenylpyridin-2-amine;
methyl 2-(2-amino-5-phenylpyridin-3-yl)-1H-benzimidazole-6-carboxylate;
2-(2-amino-5-phenylpyridin-3-yl)-1H-benzimidazole-6-sulfonamide;
3-(6-fluoro-1H-benzimidazol-2-yl)-5-phenylpyridin-2-amine;
3-(4-methyl-1H-benzimidazol-2-yl)-5-phenylpyridin-2-amine;
methyl2-[2-amino-5-(3-methoxyphenyl)pyridin-3-yl]-1H-benzimidazole-6-carboxylate;
3-(1H-benzimidazol-2-yl)-5-(3-methoxyphenyl)pyridin-2-amine;
2-[2-amino-5-(3-methoxyphenyl)pyridin-3-yl]-1H-benzimidazole-6-sulfonamide;
5-(3-methoxyphenyl)-3-(4-methyl-1H-benzimidazol-2-yl)pyridin-2-amine;
3-(5-chloro-6-fluoro-1H-benzimidazol-2-yl)-5-(3-methoxyphenyl)pyridin-2-amine;
2-[2-amino-5-(3,4,5-trimethoxyphenyl)pyridin-3-yl]-1H-benzimidazole-6-sulfonamide;
2-[2-amino-5-(3-cyanophenyl)pyridin-3-yl]-1H-benzimidazole-6-sulfonamide;
2-[2-amino-5-(4-fluorophenyl)pyridin-3-yl]-1H-benzimidazole-6-sulfonamide;
2-[2-amino-5-(4-methoxyphenyl)pyridin-3-yl]-1H-benzimidazole-6-sulfonamide;
3-(6-fluoro-1H-benzimidazol-2-yl)-5-(4-fluorophenyl)pyridin-2-amine; and 5-(4-fluorophenyl)-3-(4-methyl-1H-benzimidazol-2-yl) pyridin-2-amine;
or a salt thereof.

16. A pharmaceutical composition, comprising: a therapeutically effective amount of a compound as claimed in claim 1, or a salt thereof and one or more of pharmaceutically acceptable carriers, diluents and excipients.

17. A pharmaceutical composition, comprising: a therapeutically effective amount of a compound as claimed in claim 15, or a salt thereof and one or more of pharmaceutically acceptable carriers, diluents and excipients.

* * * * *